United States Patent [19]
Stella

[11] Patent Number: 5,224,500
[45] Date of Patent: Jul. 6, 1993

[54] RECIPROCATING FLOSSER AN TOTAL DENTAL HYGIENE

[76] Inventor: Carl J. Stella, 164 Ridge Rd., Bristol, Conn. 06010

[21] Appl. No.: 729,697

[22] Filed: Jul. 15, 1991

[51] Int. Cl.$^5$ .......................................... A61C 15/00
[52] U.S. Cl. .................................................. 132/322
[58] Field of Search .............. 132/322, 323, 324, 325, 132/309

[56] References Cited

U.S. PATENT DOCUMENTS

| | | | |
|---|---|---|---|
| 1,815,408 | 7/1931 | Jordan | 132/323 |
| 3,667,483 | 6/1972 | McCabe | 132/322 |
| 3,759,274 | 9/1973 | Warner | 132/322 |
| 3,847,167 | 11/1974 | Brien | 132/322 |
| 4,235,253 | 11/1980 | Moore | 132/322 |
| 4,458,702 | 7/1984 | Grollimund | 132/322 |
| 4,586,521 | 5/1986 | Urso | 132/323 |
| 4,706,695 | 11/1987 | Urso | 132/322 |
| 4,880,382 | 11/1989 | Moret et al. | 132/309 |
| 5,016,660 | 5/1991 | Boggs | 132/322 |

*Primary Examiner*—Cary E. O'Connor

[57] ABSTRACT

A flosser which holds the floss between two (2) unequal length prongs located in the head piece. The floss moves back and forth by a motor. When the floss is placed between the teeth and laterally moved forty-five degrees, the floss will clean between and the opposite sides of the teeth. When removed and rotated 180 degrees and placed between the same teeth, it will now clean the opposite sides of the same teeth, resulting in cleaning the four sides of the teeth. The head is detachable so that a separate round toothbrush with a guard on half of it will be able to brush in between the teeth. The top teeth are cleaned with the motor operating counterclockwise, the bottom teeth cleaned with the motor operating clockwise. However, due to its reversability, the motor may be operated in either direction as desired.

A head with the following attachments:

A small, round, pointed brush used to clean placque at the gum line

A round rubber or plastic cup to hold polish rotating at a low rpm to brighten teeth A rubber or plastic gum massager may also be placed on this head A separate head which operates a water pulser to remove solids from between the teeth which operates on an offset cam causing water to be squirted out in small bursts.

9 Claims, 2 Drawing Sheets

RECIPROCATING FLOSSER AN TOTAL DENTAL HYGIENE

BACKGROUND OF INVENTION

Dentists are constantly urging their patients to floss their teeth, particularly those in the back of the mouth, to reduce and/or prevent disease to the teeth and gums. During flossing, it is quite difficult to floss properly using their fingers, consequently most people will not floss their teeth.

Many devices have been patented whereby hand-held "Y" units or motor-driven units have been advanced. To date, there is not a single flosser available to the public which is both motor-driven and inexpensive, and no body which has separate heads to do a total dental hygienic care.

SUMMARY OF INVENTION

This invention is a hand-held motorized dental flosser, which is constructed with two (2) arms of unequal length. The arms are constructed of a plastic which is pliable and maintains pressure on the dental floss to keep it taut. When the floss is placed between the teeth and the flosser is rotated laterally, the floss will clean between and the sides with a reciprocating action. When the flosser is removed, turned upside-down and replaced between the same teeth, the opposite sides of the same teeth are cleaned. A storage spool of floss is located in the detachable head, one head for each person. The motor-driven body also has the following heads:

A round tooth brush that rotates around instead of back and forth

A pointed brush which will accommodate a rubber or plastic gum massager and/or cleaner/polisher.

Construction of the reciprocating dental flosser is very simple, thereby making it simple to manufacture, which further results in a very inexpensive device, providing total dental care.

BRIEF DESCRIPTION OF THE DRAWINGS

The following drawings are ILLUSTRATIONS ONLY of the preferred embodiments of the invention.

DESCRIPTION OF THE INVENTION IN ITS PREFERRED EMBODIMENT

Figure 1:
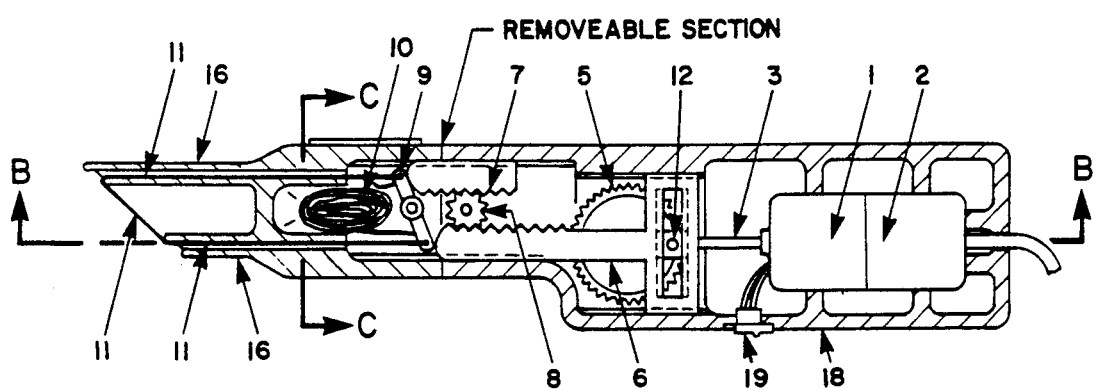
FIG. 1 is a top view of the motorized flosser embodying the invention

Referring to the drawing and FIG. 1, which is the top view of the invention, showing the main body (18) and the detachable head (17). The main body contains a reversible variable speed motor (1) and a rechargeable battery (2). The motor (1) drives a bevel gear (4) from the shaft (3). The beveled gear (5) operates the rack (6) in a back and forth motion driven by the pin (12), which is attached to the beveled gear (5). As the gear (5) turns, the pin (12) moves up and down causing the rack (6) to move back and forth.

The rack (6) moves the pinion gear (8), which in turn drives the rack (7). The switch (19) turns the motor (1) on and off.

A shaft (20) has a bevel gear (21) (28) on each end. Bevel gear (28) meshes with beveled gear (5) whereby beveled gear (21) is rotated when the motor is activated. The beveled gear (21) thereby drives the detachable accessories such as the toothbrush (FIG. 6), pointed toothbrush (FIG. 8), the cleaner/polisher (FIG. 9), the gum messager (FIG. 10), and the water pulsator (FIG. 11), by engaging the beveled gear located within the head of each detachable accessory.

The detachable head (17) is constructed of a nylon-type material due to its ability to allow the prongs (16) to be a spring-like. The springiness of the prongs (16) allows the floss (11) to be maintained taut. The spool of floss (10) is unrolled and attached to the bar (9), inserted onto the "V" shaped section of the bar (9). When the racks (6) (7) and the pinion gear (8) move, they in turn move the bar (9) back and forth, causing the dental floss to move.

Figure 2:
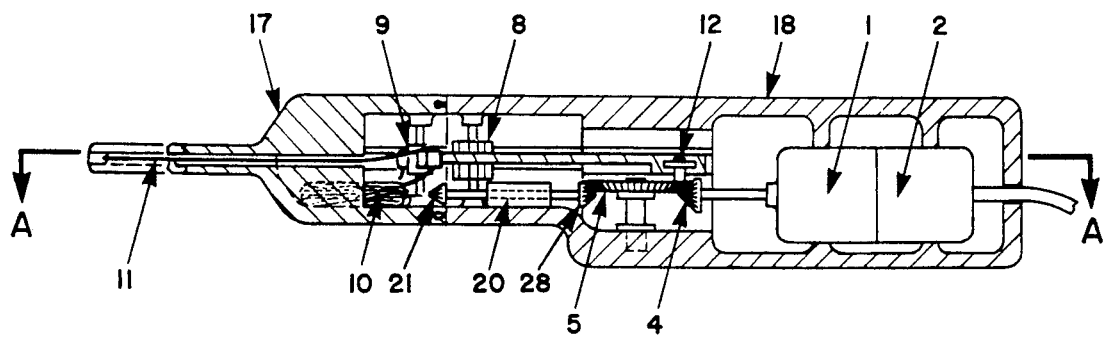
FIG. 2 is a side view of the embodiment

FIG. 2 is a side view of the invention, which illustrates the arrangement of the beveled gears (4) (5) (20), the attachment pin (12), the pin (12), the pinion gear (8), as well as the storage area for the dental floss (10).

Figure 3:
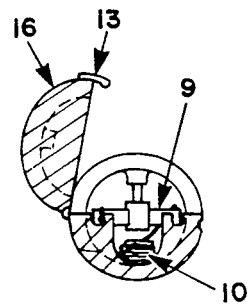
FIG. 3 is a cross-section of the embodiment showing storage of the floss and how the detachable head opens

FIG. 3 is cross-section of the detachable head (17) which contains the location of the floss (10) and the bar (9). The upper half shows the hinged portion (16), having a latch (13), where the replacement and threading of the floss is accomplished.

Figure 4:
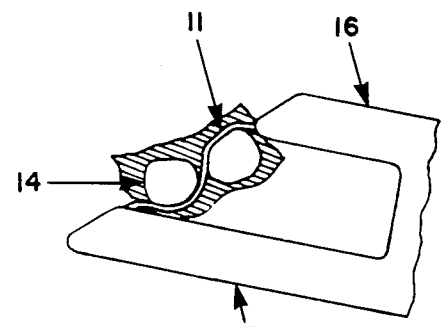
FIG. 4 shows how the floss will clean between and the sides of the teeth

FIG. 4 shows the configuration of the dental floss after the floss was placed between the teeth and the whole body (17) (18) was rotated 45° thereby cleaning not only between the teeth, but the sides as well.

Figure 5:
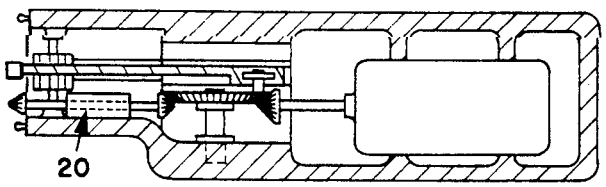
FIG. 5 is the motorized portion of the embodiment

FIG. 5 is the main motorized body.

Figures 6, 7:
FIG. 6 shows the round tooth brush
FIG. 7 is an end-view of the round tooth brush with guard

FIG. 6 is the toothbrush (22) which is round having a guard (23) on a portion of the circumference of the toothbrush.

FIG. 7 is the end-view of the round toothbrush.

Figure 8:
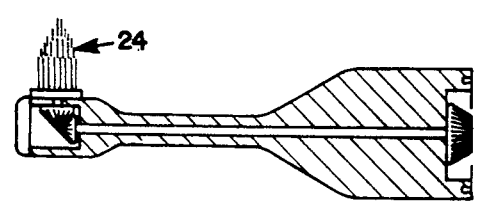
FIG. 8 is the head with the removable round pointed brush which is attached to the cam

FIG. 8 shows the pointed toothbrush (24) which may be attached to the head in FIG. 6.

Figures 9, 10:
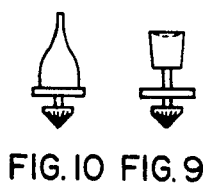
FIG. 9 is the removable cleaner/polisher which also attaches to the cam
FIG. 10 is the removable gum massager which attaches to the cam

FIG. 9 is the round cleaner/polisher.

FIG. 10 is the gum massager.

Figure 11:
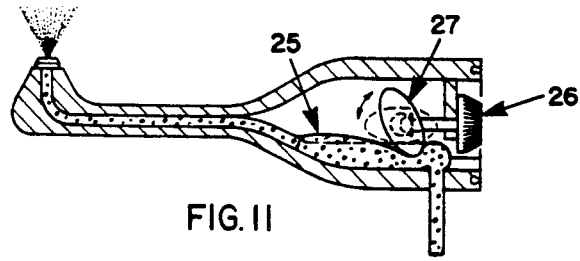
FIG. 11 is the water pulsor

FIG. 11 is the water pulsator that attaches to the main body. The head includes a flexible tube (25) through which fluid flows. A bevel gear (26) is driven by bevel gear (21). As bevel gear rotates the egg shaped roller (27) impinges upon the tube (25) to propel the water there to provide a pulsating stream of water.

I claim:

1. A dental hygiene device comprising:
   (A) a main body having therein;
      (a) a rechargeable battery,
      (b) a motor connected to said battery,
      (c) drive means, connected to said motor, for moving a rack, mounted for longitudinal movement within said body,
      (d) a shaft having a first bevel gear on one end and second bevel gear on the other end, wherein said drive means engages said first gear thereby causing the shaft and the second gear to rotate;

(B) a head piece adapted to be removably attached to the main body comprising:
  (a) a pair of prongs being of unequal length,
  (b) a bar pivotally mounted, between its ends of prongs; whereby, when the headpiece is attached to the main body, the rack abuts one of the ends of the bar to pivot said bar back and forth when motor is on, thereby imparting a reciprocating motion to said floss.

2. The dental hygiene device according to claim 1, further comprising a plurality of accessories adapted to be detachably connected to said main body, each accessory comprising a head and a beveled gear adapted to be driven by the second gear when the accessory is attached to said main body.

3. The dental hygiene device according to claim 2, wherein one of the heads includes a round brush drivably connected to the beveled gear, and a guard.

4. The dental hygiene device according to claim 3, wherein said motor is reversible and said round brush may by rotated either clockwise or counterclockwise by reversing the motor.

5. The dental hygiene device according to claim 2, wherein one of the heads includes a plurality of removably attachable cleaning devices adapted to be driven by the beveled gear, said cleaning devices including:
  (a) a pointed toothbrush,
  (b) a gum massager, and
  (c) a round polisher/cleaner.

6. The dental hygiene device according to claim 2, wherein one of the heads comprises a water pulsator for delivering water, in a pulsating manner, to the oral cavity.

7. The dental hygiene device according to claim 1, wherein said motor is a variable speed motor and is reversible.

8. The dental hygiene device according to claim 1, wherein said prongs are made of pliable material that will bend during use so that a greater surface area of the teeth is cleaned.

9. The dental hygiene device according to claim 1, wherein said floss comprises a spool of floss and the headpiece comprises a hinged access door to allow replacement of said spool.

* * * * *